United States Patent [19]
Lee et al.

[11] Patent Number: 5,388,586
[45] Date of Patent: Feb. 14, 1995

[54] METHODS AND APPARATUS FOR SENSING INTRACARDIAC SIGNALS FOR AN INPLANTABLE CARDIAC PACEMAKER

[75] Inventors: Chik-Yam Lee, Arcueil; Laurent Claudon, Heillecourt; Renzo D. Molin, Bagneux, all of France

[73] Assignee: ELA Medical, Montrouge, France

[21] Appl. No.: 172,847

[22] Filed: Dec. 23, 1993

[30] Foreign Application Priority Data

Dec. 23, 1992 [FR] France ................ 92 15661

[51] Int. Cl.⁶ ............................ A61B 5/0452
[52] U.S. Cl. ............................ 128/704; 128/903
[58] Field of Search ............ 128/696, 697, 702, 704, 128/903; 607/9, 18, 27; 341/143; 375/27, 28

[56] References Cited

U.S. PATENT DOCUMENTS

| | | | |
|---|---|---|---|
| 4,596,252 | 6/1986 | Nelson | 128/419 PG |
| 4,692,719 | 9/1987 | Whigham | 607/9 |
| 4,708,144 | 11/1987 | Hamilton et al. | 128/419 PG |
| 4,974,589 | 12/1990 | Sholder | 128/419 PG |
| 5,024,221 | 6/1991 | Morgan | 128/419 PG |
| 5,055,843 | 10/1991 | Ferguson, Jr. et al. | 341/143 |
| 5,273,049 | 12/1993 | Steinhaus et al. | 128/696 |

FOREIGN PATENT DOCUMENTS

| | | | |
|---|---|---|---|
| WO9110472 | 7/1991 | European Pat. Off. | A61N 1/36 |
| 3226345A1 | 7/1982 | Germany | A61N 1/36 |

*Primary Examiner*—George Manuel
*Attorney, Agent, or Firm*—Davis Hoxie Faithfull & Hapgood

[57] ABSTRACT

A circuit for use in an implantable cardiac pacemaker for use in processing intracardiac signals and methods of processing such signals. The circuit includes a passive filter 1 has a bandwidth of 0.1 to 80 Hz approximately. An amplifier 2 with switched capacitors presents at the output a dynamics of 0.8V approximately and a gain lower than 50. An analog-to-digital converter 3 with delta modulation, which is controllably variable in step and functions at two frequencies, one of 1 kHz approximately, the other of 4 kHz approximately. The circuit may be used for both processing said signals to identify spontaneous cardiac events and to telemeter an intracardiac ECG.

41 Claims, 9 Drawing Sheets

METHODS AND APPARATUS FOR SENSING INTRACARDIAC SIGNALS FOR AN INPLANTABLE CARDIAC PACEMAKER

BACKGROUND OF THE INVENTION

The present invention concerns implantable cardiac pacemakers, more specifically signal processing methods and apparatus for detecting intracardiac signals for controlling pacing operation and for monitoring the intracardiac electrocardiogram (ECG) externally.

Most cardiac pacemakers function according to the pacing mode that is inhibited: a stimulation pulse is delivered only if no spontaneous activity is detected during a period of sensing corresponding to the duration of a cardiac cycle (800 ms for a normal rhythm of 75 cpm). This mode of functioning allows an economy of energy, that is to say an increase of the longevity of the pacemaker.

An inhibited pacing mode also allows, from the physiological point of view, to avoid a competition between the spontaneous rhythm of the patient and the frequency of stimulation of the cardiac pacemaker. Competition is not avoided in an asynchronous pacing mode.

The cardiac activity, represented by a variation of cell potential of the myocardium, is sensed in a cardiac pacemaker by means of electrodes placed on the wall of the atrium and/or the ventricle, according to the type of the cardiac pacemaker (AAI, VVI, DDD).

Some problems linked to the sensing are due to the perturbation potentials created by the pacemaker itself. Indeed, stimulation pulses provoke important variations of the cell potential, in the stimulated cardiac chamber as well as in the non stimulated chamber. The sensing of a stimulation pulse in the cardiac chamber that is not stimulated is a particular problem during the ventricular sensing period following an atrial stimulation. Indeed, it is necessary to sense the ventricle as soon as possible after the stimulation so as to verify the good atrial-ventricular conduction.

SUMMARY OF THE INVENTION

It is, therefore, an object of the present invention to remedy the aforementioned problems, and provide for sensing signals corresponding to the cell potential that do not confuse a sensed signal deflection due to a stimulation with a sensed signal deflection due to a spontaneous event.

Another object of the invention is to provide an implantable cardiac pacemaker that uses the same electronic circuit for sensing the spontaneous cardiac activity and the transmission of the intracardiac ECG to the outside.

Another object of the invention is to provide an implantable cardiac pacemaker that faithfully senses a deflection due to a stimulation, so as to measure correctly the parameter of efficiency, or inefficiency, of the stimulation. The efficiency (or efficiency) measurement then can be used to operate an algorithm of adaptation of energy of the stimulation, i.e., adjust the stimulation energy.

Another object of the invention is to provide an implantable cardiac pacemaker that has an automatic adjustment of the signal sensitivity so as to take into account the evolution in time of the form of the sensed signal.

Another object of the invention is to anticipate an automatic adjustment of the period of blanking according to the importance of the diaphonie (cross-talk) following on the signal.

Broadly, the invention concerns an implantable cardiac pacemaker having a circuitry for sensing variations of potential generated by the spontaneous and stimulated cardiac activity, and which is susceptible to be used to transmit, by telemetry to the exterior, the intracardiac electrocardiogram (ECG).

One aspect of the present invention is directed to an apparatus for use in an implantable cardiac pacemaker in which a circuit for the acquisition and detection of the intracardial electronic activity comprises a passive filter, an amplifier, an analog to digital converter (preferably of the delta modulation type), a microprocessor, and an algorithm to insure the detection of spontaneous cardiac events. One such apparatus is characterized by:

(a) the filter being a band pass filter having a frequency pass range spreading from 0.1 to 80 Hz approximately;

(b) the amplifier having switched capacitors and presenting to the output a dynamic range of 0.8V approximately and a low gain that is lower than 50; and (c) the analog-to-digital converter has a variable sampling frequency and a variable step magnitude (resolution).

The electronic signal acquisition and detection circuit has a large bandwidth, a low gain and a large dynamic range, which provides for the detection of spontaneous atrial and/or ventricular events, the measure of the efficiency parameter of the stimulation, and the transmission of an intracardial ECG by telemetry. The output of this circuit are digital values (digital signals) corresponding to the intracardial cardiac electrical activity of the patient. The terms "digital values" and "digital signals" are used interchangeably.

In other embodiments, the invention also includes an automatic adjustment of the period of blanking and/or an automatic adjustment of the sensitivity. These are preferably implemented by software processing of the obtained digital values. In addition, the analog-to-digital converter preferably functions at two sampling frequencies, one of approximately 1 kHz, the other of approximately 4 kHz.

Other aspects of the present invention include the following. The command of the frequency change and of the step change of the analog-to-digital converter is realized by comparison of the absolute value of the variation of amplitude of the processed digital signals that are sensed (i.e., detected, measured or monitored) during a duration of from 6 to 12 ms, preferably 9 ms, with a threshold called threshold of acceleration.

The detection of an atrial or ventricular spontaneous cardiac event is realized by a comparison of the absolute value of the variation of amplitude of the digital signals sensed during a duration of 6 to 12 ms, preferably 9 ms, with a threshold called threshold of detection.

The function of detection of a ventricular or atrial cardiac event is preferably realized by numerical processing of the digital signals with a dedicated microcontroller.

The sign of a variation of amplitude of the digital signals sensed during a duration of 6 to 12 ms, preferably 9 ms, before the end of the absolute refractory period (ARP), where the absolute value of the amplitude variation is greater than the threshold of detection, is memorized. The detection, after the ARP, of a spontaneous event is then indicated only if the absolute value of the variation of amplitude of the digital signals sensed during a duration of 6 to 12 ms, preferably 9 ms, is greater than the threshold of detection, and if the sign of this amplitude variation is of opposite sign to the sign memorized during the ARP.

The duration of the ventricular blanking interval is adjustable manually or automatically. In the case of an automatic adjustment, the duration of blanking is adjusted to each atrial stimulation according to the amplitude of the cross-talk. In the course of an automatic adjustment of the blanking interval, the end of the blanking interval is determined as follows. First, the sign of the amplitude variation of the digital signals sensed during a duration of from 6 to 12 ms is determined for each of a series of consecutive durations. The end of the blanking period is then determined to be the time when the sign between two consecutive durations first inverts.

The amplitude of the deflection of the ventricular signal following an atrial stimulation is measured at the end of the blanking period. The sign of this deflection is memorized. If the amplitude of this deflection is greater than the threshold of detection at the end of the blanking period, then the absolute value of the amplitude variation of the ventricular signal sensed during a duration of 6 to 12, preferably 9 ms, being greater than the threshold of detection, and the sign of the amplitude variation being identical to the memorized sign of the deflection will be considered alone as due to the presence of a ventricular event. In the contrary case, i.e., when the amplitude of deflection is less than the detection threshold, the detection of a ventricular event is realized based on the absolute amplitude variation criteria without the constraint of sign.

During an automatic sensitivity adjustment, a search of the absolute value of the maximal amplitude variation of the signal sensed during a duration of 6 to 12 ms, preferably 9 ms, begins on a detection of a spontaneous atrial and/or ventricular cardiac event, and extends a given period, preferably 48 ms. During an automatic adjustment of the sensitivity, an initial sensitivity is programmable by the physician. In the case of a cardiac stimulation, the programmed value is multiplied by a factor, preferably 1/0.375, and is used in place of the maximal amplitude variation memorized after a detection.

In one embodiment, during an automatic adjustment of the sensitivity, the new threshold of detection is selected as a certain percentage, preferably 37.5%, of the average of the last eight determined maximal values of the amplitude variation of the digital signal sensed during a duration, e.g., 9 ms, which are sensed for each spontaneous event.

BRIEF DESCRIPTION OF THE DRAWINGS

Further features and advantages of the invention will be apparent upon consideration of the following detailed description of a preferred embodiment of the invention, taken in conjunction with the accompanying drawings, in which like reference numerals refer to like elements, and in which.

DETAILED DESCRIPTION OF THE INVENTION

Figure 1:
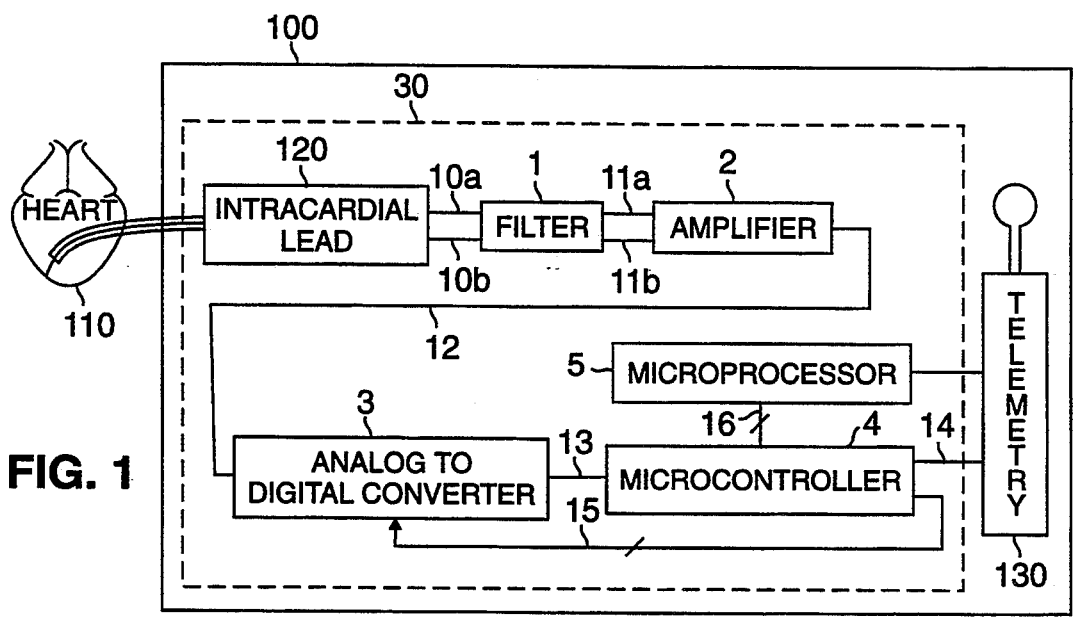
FIG. 1 is a simplified circuit diagram of the electronic acquisition circuit of the cardiac activity in an implantable cardiac monitoring device according to an embodiment of the invention.

Referring to FIG. 1, the electronic circuit 30 for acquiring and detecting the cardiac signal includes a passive filter 1 having large bandwidth, an amplifier 2 with switched capacitors and low gain, an analog to digital a converter 3 with variable frequency and variable steps, a microcontroller 4 which performs the functions of detection and processing of the cardiac activity signal and allows for adapting to phenomenon due to stimulations and to the cross-talk, and measuring the amplitude of the event detected, and a microprocessor 5, which supervises the functioning of a cardiac monitoring device 100, such as a pacemaker coupled to the patient's heart 110 by intracardial leads 120, and insuring the automatic adjustment function of sensitivity.

Figure 2:
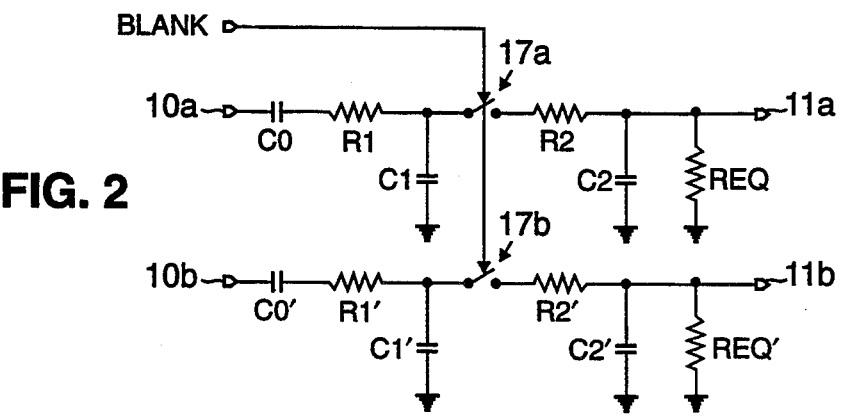
FIG. 2 is a circuit diagram of an embodiment of the passive filter of FIG. 1.
Figure 3:
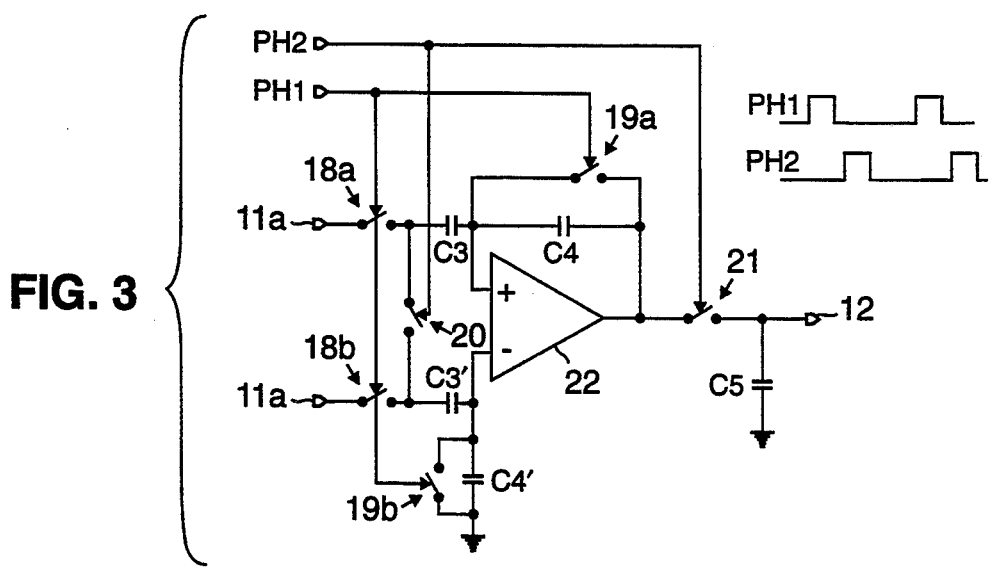
FIG. 3 is a circuit diagram of an embodiment of the amplifier of FIG. 1.

In FIGS. 1–3, references 10a, 10b, 11a, 11b, and 12 to 16 designate the electrical connections or leads. Reference 14 also symbolizes the output of the electronic acquisition and detection circuit 30.

Referring to FIGS. 1 and 2, a preferred circuit diagram of filter 1 is shown. Signals coming from intracardial leads 120 are provided to filter 1 at input leads 10a and 10b. The filtered signals are output at output leads 11a and 11b. The input 10a is preferably connected to the distal part of the intracardiac lead while the input 10b is connected is to the case of the pacemaker 100 during unipolar sensing and to the proximal part of the intracardiac lead 120 during a bipolar sensing. A switch 17a, 17b, which is commanded by a command signal BLANK, allows to isolate controllably the acquisition circuit in order, notably to protect electronic components during the delivery of a stimulation impulse.

Referring to the filter circuit portion for input lead 10a, the low pole frequency of filter 1 is set by a capacitor CO and the resistance Req at the input of amplifier 2, preferably situated at about 0.1 Hz. A first high pole frequency is provided by a resistance R1 and a capacitor C1, preferably situated at about 80 Hz. A second high pole frequency is provided by a resistance R2 and a capacitor C2, preferably in the range of 3 kHz. The filter characteristics for the input lead 10b are the same as for lead 10a and are illustrated in FIG. 2 by the use of the same reference numerals having "primes".

The low frequency pole is selected to obtain two advantages. First, it does not alter stimulation signals, so that an accurate measure of the parameter of efficiency of stimulation can be obtained. Second, it does not alter low spontaneous signal frequency (extrasystoles ES, T-wave, etc...) so that this acquisition circuit also can be used for sensing an intracardial electrocardiogram (ECG) for transmission out of the pacemaker (or cardiac monitoring device 100 (e.g., a pacemaker, cardioverter, or defibrilator or other implantable device), by telemetry circuit 130.

The high frequency pole of 80 Hz is selected because it corresponds to the highest frequency of sensed cardiac signals (atrial or "P" waves and/or ventricular or "R" waves). The second pole at 3 kHz is provided for protection against electromagnetic interference and to comply with appropriate safety standards, such as the European norm NF EN50 061, on the safety of the implantable cardiac pacemakers.

Referring to FIG. 3, a circuit diagram of amplifier 2 with switched capacitors is shown. The switched capacitor principle is used to reduce the number of external electronic components, by an integration of the former in an integrated circuit chip, so as to reduce the size of the electronic circuit in the implanted pacemaker. Amplifier 2 with switched capacitors comprises a differential amplifier 22, capacitors C3, C3', C4, C4' and C5, and switches 18a, 18b, 19a, 19b, 20 and 21. Switches 18a to 19b are commanded by a control signal signal Ph1 provided by a first clock source (not shown). Switches 20 and 21 are commanded by a control signal signal Ph2 provided by a second clock source (not shown).

The two distinct clock sources deliver signals Ph1 and Ph2 respectively, such that they are never active simultaneously, as represented on the upper right part of FIG. 3. During the active phase of signal Ph1 of the first clock source, switches 18a to 19b are closed and switches 20 and 21 are opened. As a result, capacitors C3 and C3' are each loaded to the voltage coming from filter 1, on leads 11a and 11b respectively and capacitors C4 and C4' are unloaded. At the end of the active phase of signal Ph1, switches 18a to 19b are opened and the charges on capacitors C3 and C3' distribute respectively between capacitors C3 and C4 on the one hand, and capacitors C3' and C4' on the other hand.

During the active phase of signal Ph2 of the second clock source, switches 20 and 21 are closed. As a result, the difference of voltage signals present on capacitors C3 and C3' is amplified by the differential amplifier 22 in the ratio C3/C4, and the result is stored on capacitor C5. The gain being realized by the ratio of the two capacities, it is possible to adjust this ratio so as to have, to the output, a maximal dynamic range.

Figure 4:
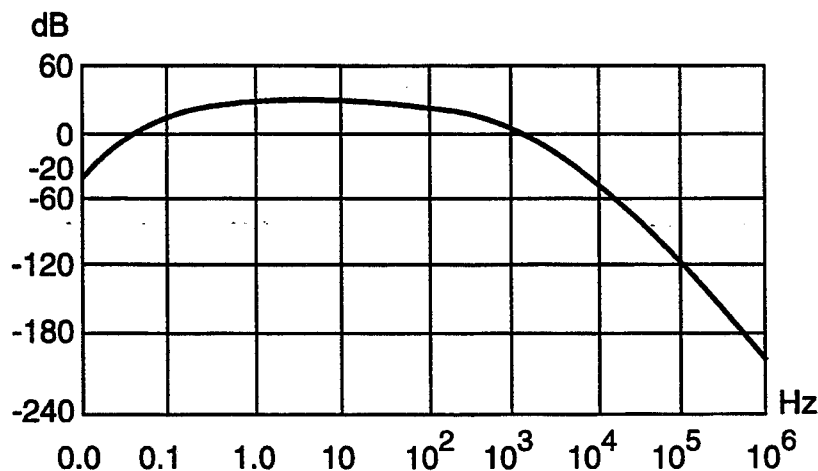
FIG. 4 is a Bode plot diagram of Hz versus dB for a circuit of the filter of FIG. 2 and the amplifier of FIG. 3.

The interest of a large dynamic range resides in the fact that the parameter of efficiency of stimulation can be more easily measured. Indeed, in accordance with the present invention, stimulation signals are not altered, neither by a filtering of the low frequencies by reason of the bandwidth of the filter 1, nor by a saturation of the amplifier 2 by reason of the choice of the amplifier gain. As examples, in case of an atrial cardiac lead, the gain can be fixed to 40 approximately, and in case of a ventricular lead, the gain can be fixed to 15 approximately. The differential gain of the totality of filter 1 and amplifier 2 is represented on FIG. 4.

Figure 5:
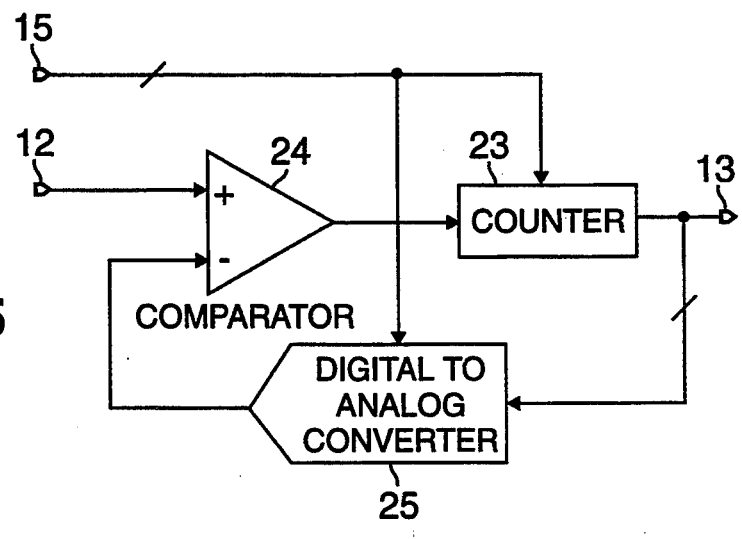
FIG. 5 is a simplified block diagram of an embodiment of the analog to digital converter with delta modulation of FIG. 1.

FIG. 5 illustrates an analog to digital converter (ADC) 3 with delta modulation, comprising a comparator 24, a counter 23, and a digital to analog converter 25. According to the principle of delta modulation, the result of a measured difference (delta) is modulated based on the amplitude of the variation of the input signals. The main disadvantage of an ADC with delta modulation is that it is not able to follow correctly a signal presenting a rapid amplitude variation due to the fact that the digitization been made by increment or decrement of a step of the counter at each sampling. This problem is overcome by the present invention which provides that the sampling frequency and the step magnitude of ADC 3 can be modified as a function of variations of the signal sensed. Indeed, the signal detection algorithm, described in more detail below, responds to variations of amplitude of the signal coming from the cardiac lead. If the signal coming from the myocardium does not present variations, the analog to digital conversion is realized using a "basic" frequency of, for example, 1 kHz. On the other hand, when the base line of the signal presents variations, due, for example, to the presence of an event or a stimulation, the ADC functions to convert the signal using a more significant "accelerated" frequency, for example, 4 kHz. The higher frequency allows to follow correctly the sensed analog signal for conversion.

The ADC step also can be modified according to the programmed sensitivity, that is to say that the magnitude of the step can be equal to 1 LSB (least significant bit), or more than 1 LSB, for example, to 2, 4 or 8 LSB. Providing ADC 3 with a small step magnitude, for example, equal to 1 or 2 LSB, allows one to obtain a high precision, whereas using a greater step magnitude allows one to obtain a greater dynamic range of signal processing. A compromise thus has to be found between the desired sensitivity and precision that one desires to obtain. In one embodiment according to the invention, a table of conversion is used to select the step magnitude corresponding to the basic frequency and the step magnitude corresponding to the accelerated frequency for each sensitivity.

The advantage of such principle is the adaptation of the frequency and the step of the ADC as a function of the signal to be converted, and, indeed, the adaptation of conversion to reach the desired result as appropriate in the circumstances.

Referring to FIG. 5, the signal coming from amplifier 2 arrives at input lead 12, and is read each millisecond, and the corresponding digital signal word (digital value) is output on lead 13. The command signals which control the frequency of the counting operation and the step of counting, arrive by the bus 15 from microcontroller 4. Microcontroller 4 functions in real time and is preferably dedicated to the cardiac event detection.

An algorithm of cardiac event detection is integrated in microcontroller 4. The principle of the detection algorithm is based on a study of a variation of amplitude of the digital signals during a fixed duration of between 6 and 12 ms, and preferably equal to 9 ms, as in the example described. This principle is equivalent to a calculation of the slope over 9 ms of the sensed signal. The principle of calculation of the slope of the signal coming from the cardiac activity has already been developed by D. W. Davies, as described in U.S. Pat. No. 4,905,708, to distinguish different arrhythmias.

Figure 6:
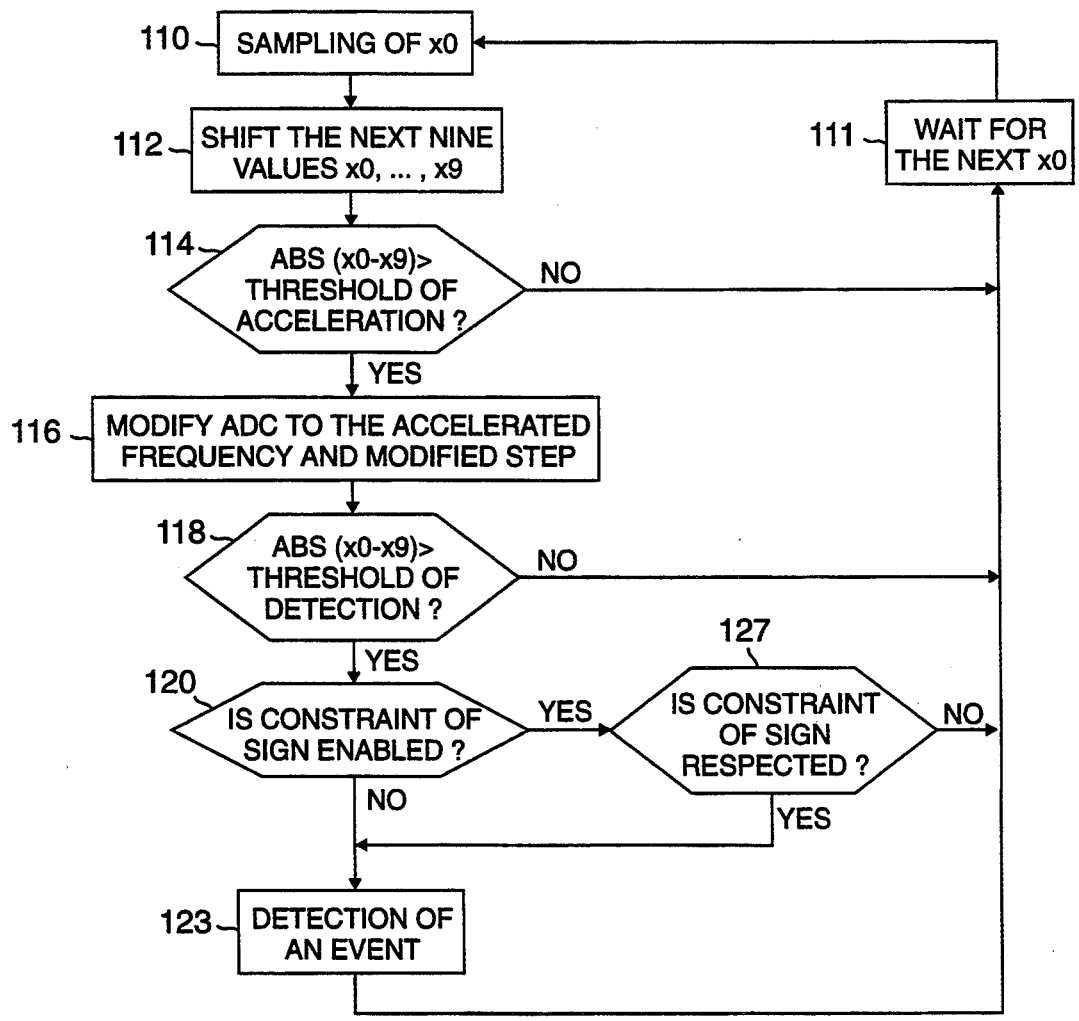
FIG. 6 is a flow chart of a routine for cardiac detection implementable in the microcontroller of FIG. 1.

FIG. 6 represents a flow chart of the main algorithm of intracardiac event detection. Concerning the constraint of sign, it is found at step 120 to be enabled (YES) or order disabled (NO). The proposed algorithm determines, for each time t of sampling, the difference between the value x0 sampled at time t and the value x9 sampled at instant (t−9). Thus, the algorithm provides for storing in memory (e.g., a shift register) the last ten samples coming from ADC 3 and shifts them by a value at each instant of sampling t, e.g., the ADC sampling interval. See steps 110 and 112 of FIG. 6.

At step 114, the absolute value of the difference (x0−x9) is calculated and compared to a first threshold called threshold of acceleration. If the acceleration threshold is exceeded, at step 116 the ADC is commanded to function using the high frequency (for example 4 kHz, as compared to a basic frequency of 1 kHz) during a predefined period, equal to 4 ms in the example described, recyclable to each passing of the threshold of acceleration. The step magnitude of counter 23 of ADC 3 also can be modified at step 116 to follow the programmed sensitivity.

At step 118, the absolute value (ABS) of the difference (x0−x9) is then compared to a second threshold called threshold of detection, corresponding to the sensitivity programmed. If this second threshold is exceeded, the detection of an event is indicated as likely.

According to the invention, to indicate the presence of a cardiac event, it is also foreseen to add, at steps 120, 122 and 123, a constraint on the sign of the difference (x0−x9), in the case where this difference is greater than the threshold of detection, in order to consider this passing of threshold as being due to the presence of a spontaneous contraction and not due to a variation of the base line of the sensed signal provoked by other phenomena. This constraint of sign is imposed only after a stimulation, and in case of cross-talk.

Modifications of frequency and step of ADC 3 are made by providing appropriate command signals on bus 15 (FIG. 5). The detection and acceleration thresholds are provided to microcontroller 4 by microprocessor 5. A detection of event is indicated in the other parts of the pacemaker by the intermediary of output signal 14 (FIG. 1).

Figure 7:
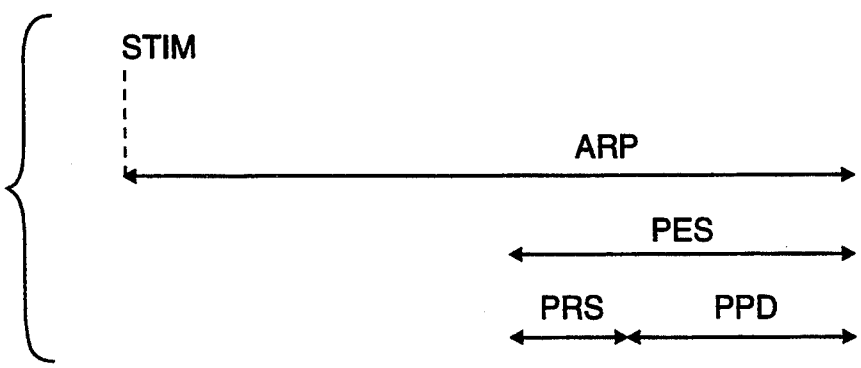
FIG. 7 is a diagram of the trapping of the signal at the end of absolute refractory period (ARP)

According to the invention, a phase of trapping of the signal is called after a stimulation. With reference to FIG. 7, in case of stimulation (Stim.), an absolute refractory period (ARP) begins in the cardiac chamber stimulated. This period whose duration is adjustable by the physician, corresponds to the period during which cells of the myocardium are refractory to all stimulation. In the beginning of the ARP, ADC 3 as well as the algorithm of detection are stopped so as to minimize the consumption of energy. Another period called period of study of the signal (PES) is included in the ARP as indicated in FIG. 7. The PES further decomposes itself in two periods, called period of trapping of the signal (PRS) and period of pre-detection (PPD).

Figure 8A:
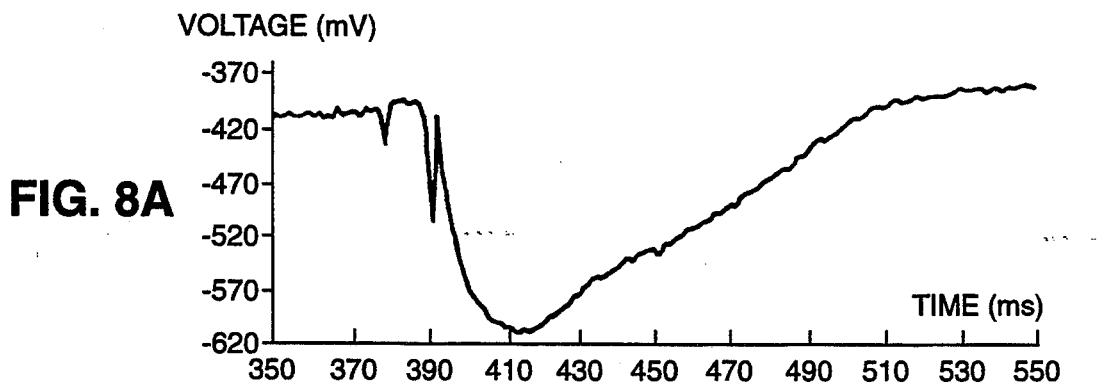
FIGS. 8A and 8B are respectively representative diagrams of a signal at the output of amplifier, that follows a cardiac stimulation, and of a signal at the output of the analog to digital converter, of the trapping at the end of ARP.
Figure 8B:
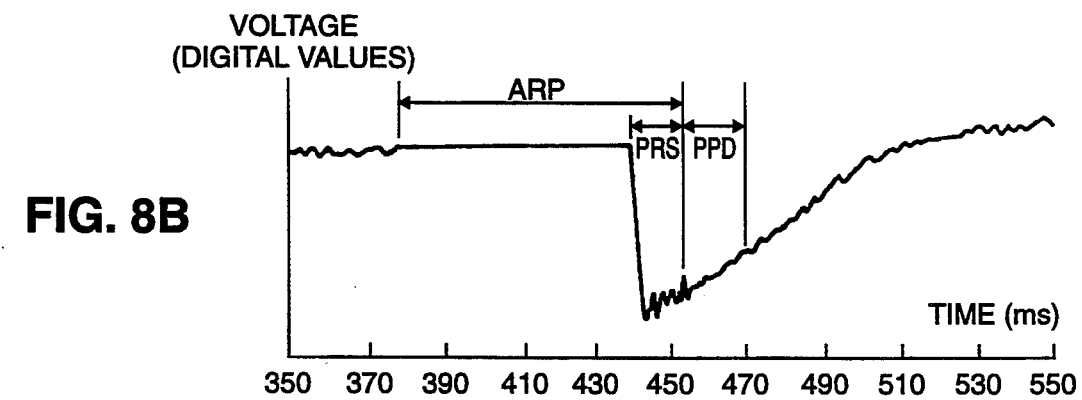

In the beginning of the PRS period, ADC 3 is set to function at the high frequency and with a step equal to 8 LSB. This type of functioning allows to recapture the important variation of the signal caused by the stimulation between the beginning of the ARP and the moment of the re-activation of ADC 3 as shown in FIG. 8. In the example described, the PRS is fixed to 16 ms, which allows to cover the whole range of ADC 3.

After the PRS interval, the PPD period begins. During the PPD period, the frequency and step of the of the ADC are controlled by the algorithm of detection, that is to say that it functions at the basic frequency of 1 kHz with a normal step (e.g., 1 LSB) and these parameters can be modified if the sensed digital signal presents variations of slope as described.

Figure 9:
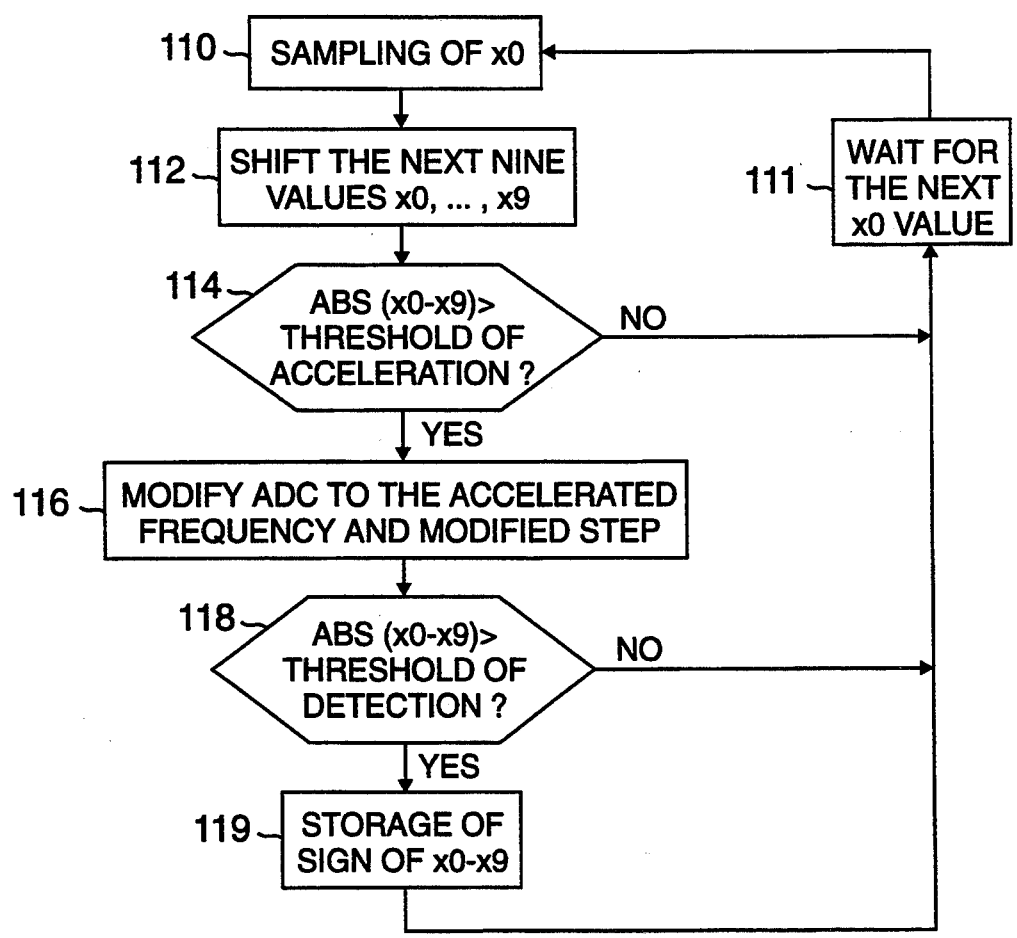
FIG. 9 is a flow chart of the signal processing at the end of ARP.

The algorithm of detection is controlled to begin functioning at the beginning of the PPD. During this period, which is fixed to 32 ms in the example described, if one or several detections occur, they are considered as being provoked by a variation of the base line of the sensed cardiac signal after a stimulation. The sign of the last difference (x0−x9) that has generated a detection during the PPD is stored as indicated at step 119 of the flow chart of FIG. 9.

After the end of the ARP, a supplementary condition, the constraint of sign, is added to consider a detection as being really provoked by an event. This condition is a test of the sign of the difference (x0−x9). Differences (x0−x9) whose sign is opposite to that stored, and whose absolute value of the amplitude is greater than the threshold of detection, are sufficient alone to be considered as being provoked by a cardiac event.

Figure 10:
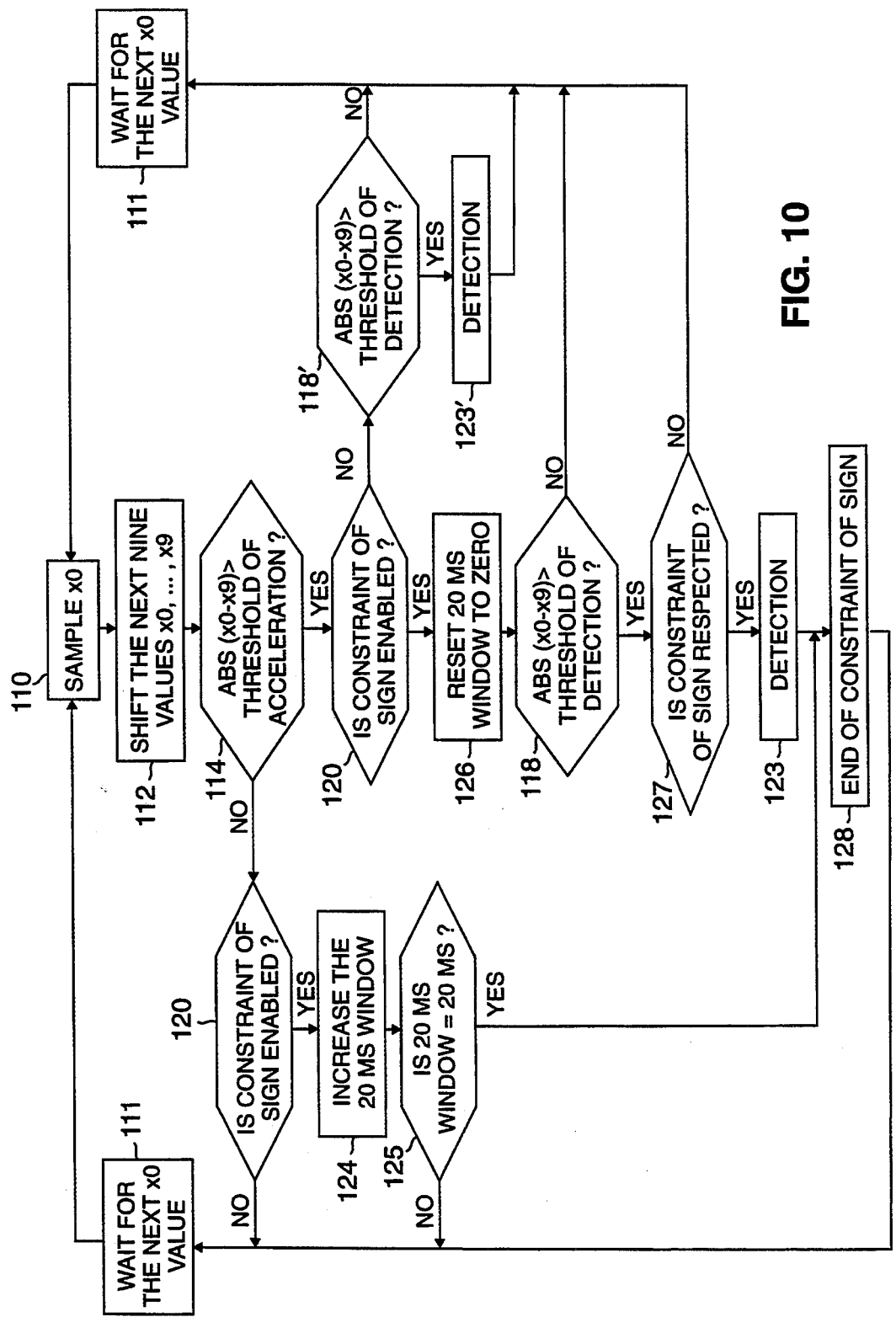
FIG. 10 is a flow chart of the signal processing of the constraint of sign according to the invention.

The test of sign is further illustrated and described by the flow chart of the FIG. 10. The constraint on the sign of the calculated slope is suppressed in the following circumstances:

(1) the absolute value of the difference (x0−x9) does not exceed the threshold of acceleration during a certain period, selected to be 20 ms in the example described (See steps 124-127, 114, 120, 124, 125 FIG. 10). This last condition indicates that the base line is practically no longer altered, (2) the absolute value of the difference (x0−x9) exceeds the threshold of detection, with a sign of the difference (x0−x9) contrary to the stored sign, which corresponds to the detection of a cardiac event (steps 114, 118, 120, 127), and (3) 400 ms after the stimulation.

Figure 11:
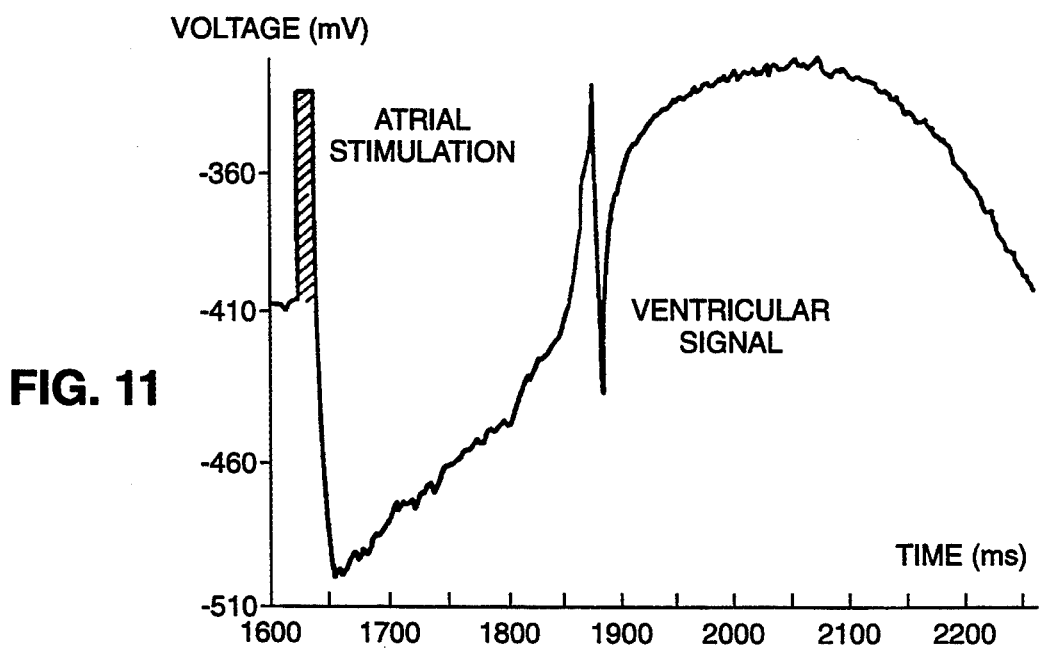
FIG. 11 is a representative diagram of a signal of cross-talk, followed by a spontaneous ventricular contraction.

According to the invention, a processing of the phenomenon of cross-talk also is taken into account. In case of atrial stimulation (ventricular), the Sensed ventricular signal (atrial) can present a deflection due to the phenomenon of cross-talk. FIG. 11 illustrates this phenomenon on the ventricular signal during an atrial stimulation, to the exclusion of the spontaneous ventricular contraction induced by the atrial stimulation, and represented between times 1850 and 1900, the ventricular signal corresponds to the cross-talk. This deflection can be more or less important according to the atrial stimulation energy, characteristics of leads (material, surface) and the mode of stimulation and sensing (unipolar, bipolar).

The phenomenon of cross-talk is described a general manner in the literature by C. D. Johnson in "Atrial Synchronous Ventricular Inhibited (VDD) Pacemaker-Mediated Arrhythmia Due to Atrial Undersensing and Atrial Lead Oversensing of Far-Field Ventricular Afterpotentials of Paced Beats: Cross-talk", *Pace*, Vol. 9, pp 710–719, and a more particular manner by W. J. Combs et al. in "Cross-Talk in Bipolar Pacemakers", *Pace*, Vol. 12, pp 1613–1621.

During an atrial stimulation, a period called "blanking" (or the "blanking" interval) begins. The duration of the blanking interval is traditionally programmed by the physician according to the cross-talk observed on an intracardial ECG.

The invention thus presents the advantage to function either with a blanking interval that is programmed, or adjusted automatically according to the importance of the cross-talk present on the sensed signal.

The U.S. Pat. No. 4,974,589 describes an automatic adjustment method of the blanking period by re-triggering a period of sensing for each ventricular detection after an atrial stimulation. The period of blanking is considered as ended if no detection is recorded during the period of sensing, with nevertheless a maximal value of the duration of blanking not to exceed, for example, 50 ms.

Whatever type of blanking is chosen (programmed or automatic), the algorithm of detection stores the value of the base line (VLB) at the moment of the stimulation, and stops. At that time a first period, called period of non sensing (PNE), begins during which the ventricular detection circuit of the cardiac pacemaker is disconnected from the leads (i.e., the signal BLANK is active (FIG. 2)). In the embodiment described, the duration of the PNE period is 14 ms. This technique is very commonly used to protect electronic components at the input to the acquisition circuit against phenomenon of oversaturization due to the stimulation.

Figure 12:
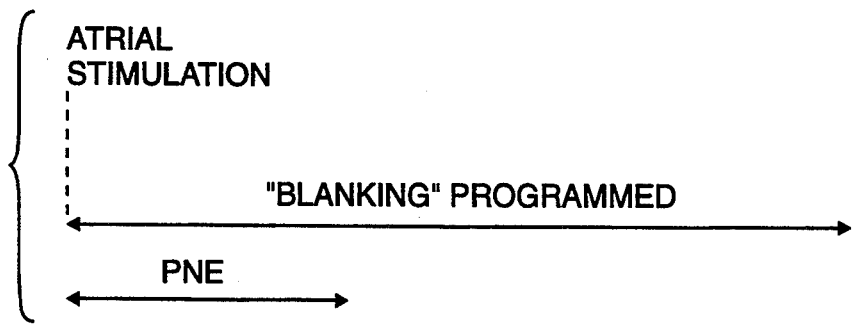
FIG. 12 is a diagram of a blanking interval programmed to be less than a duration of 32 ms.

In the following discussion, it is necessary to differentiate the programmed blanking and the automatic blanking. For a duration of blanking programmed by the physician, there are again two possible processing types:

For a short programmed blanking duration, i.e., less than 32 ms in the embodiment described, the ADC functions, beginning at the end of the PNE period, at the high frequency with a step corresponding to the programmed sensitivity and continues such functioning until the end of the blanking period (FIG. 12).

Figure 13:
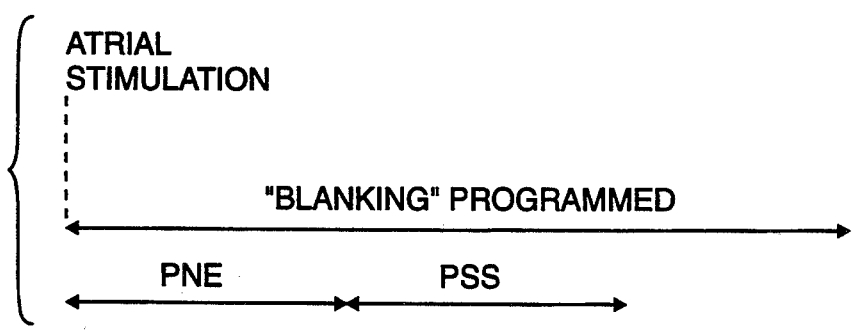
FIG. 13 is a diagram of a blanking interval programmed to be greater than a duration of 32 ms.

For a duration of blanking that is programmed greater than 32 ms, the ADC functions, beginning at the end of the PNE period, at the high frequency with a step equal to 8 LSB, and continues such functioning for a period of 16 ms, called the period of following the signal (PSS). This is used because when the physician programs a duration of blanking that is important, that means that the deflection observed also is important. By this means, it is possible to follow correctly a rapid and important variation of the signal (FIG. 13)

For a duration of blanking adjusted automatically, the ADC starts to function, beginning at the end of the PNE, at the high frequency with a step equal to 8 LSB.

Figure 14:
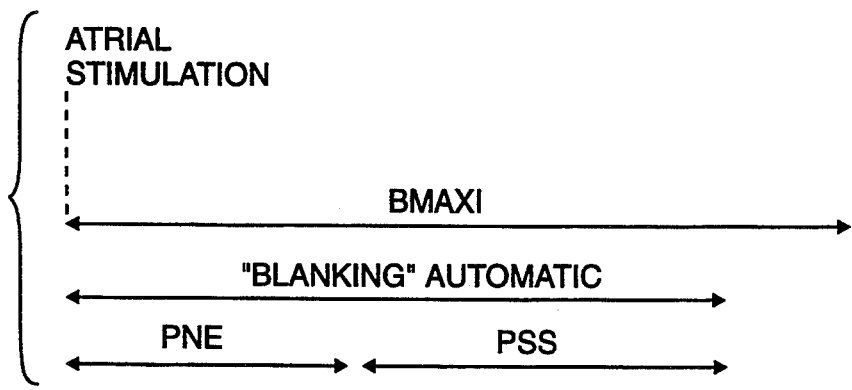
FIG. 14 is a diagram of an automatic blanking interval.

The algorithm of detection is reactivated at the end of the PNE period. At the end of the PNE period, a period called the period of following the signal (PPS) begins, during which the detection algorithm undertakes a test for the end of blanking. Once this test is validated, the period of blanking is ended (FIG. 14). The test of end of blanking is discussed below.

Figure 15:
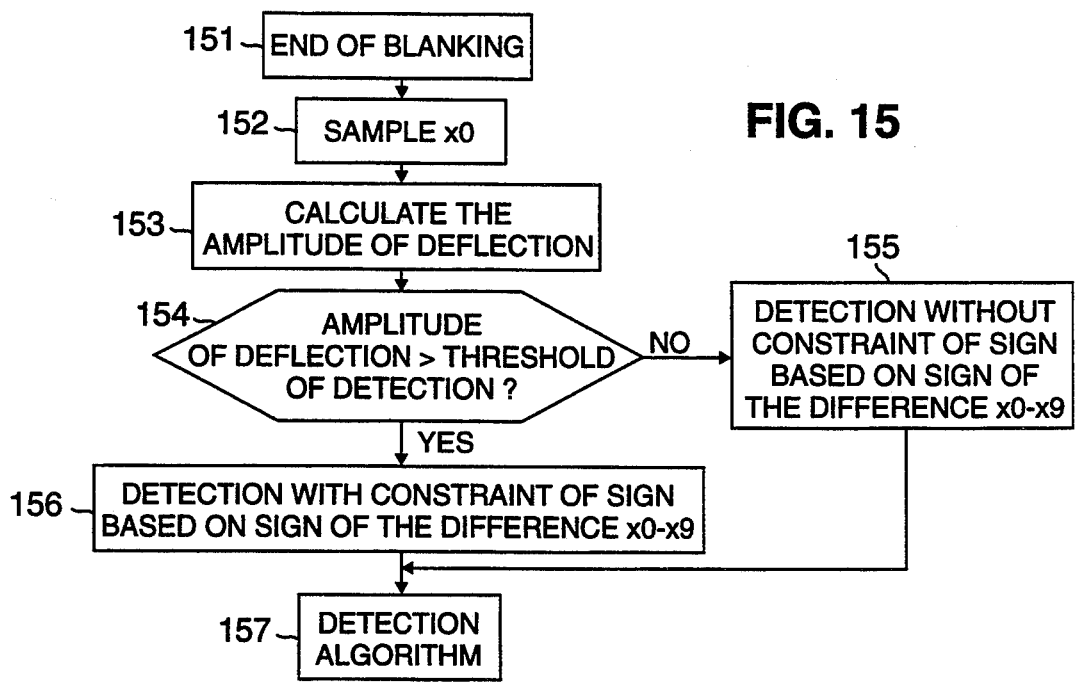
FIG. 15 is a flow chart for the test process for crosstalk.

In case of a manual adjustment of the duration of the blanking, the detection algorithm is set to begin functioning at the end of the blanking period by a command coming from microprocessor 5. The algorithm begins by taking the signal value presented to the output of ADC 3, called the value of end of blanking (VFB), and it undertakes a test of cross-talk. The test of cross-talk, with reference to FIG. 15, calculates the amplitude and the sign of the deflection of the signal at the end of the blanking interval (steps 151, 152). The amplitude and the sign are calculated at step 153 by the difference between the value VFB and the value VLB. If the absolute value of the amplitude of the deflection due to the atrial stimulation is lower than the programmed detection threshold (at step 154), then the detection routine proceeds normally without the constraint of sign (step 155). However, if the absolute value of this amplitude is greater than the programmed detection threshold, there is risk to detect a signal caused by the deflection. Accordingly, a detection of event will be indicated at this time t only if the value of the difference $(x0-x9)$ calculated at this time t is greater than the threshold, and if the sign of this difference is the same that of the deflection (step 156).

The constraint on the sign of the calculated slope is removed when during an period equal, for example, to 20 ms, the absolute value of the difference $(x0-x9)$, namely ABS $(x0-x9)$, does not exceed the threshold of acceleration (FIG. 10). This last condition indicates that the base line is practically no longer altered. This solution implies naturally that the period of blanking covers the first slope of the deflection.

Figure 16:
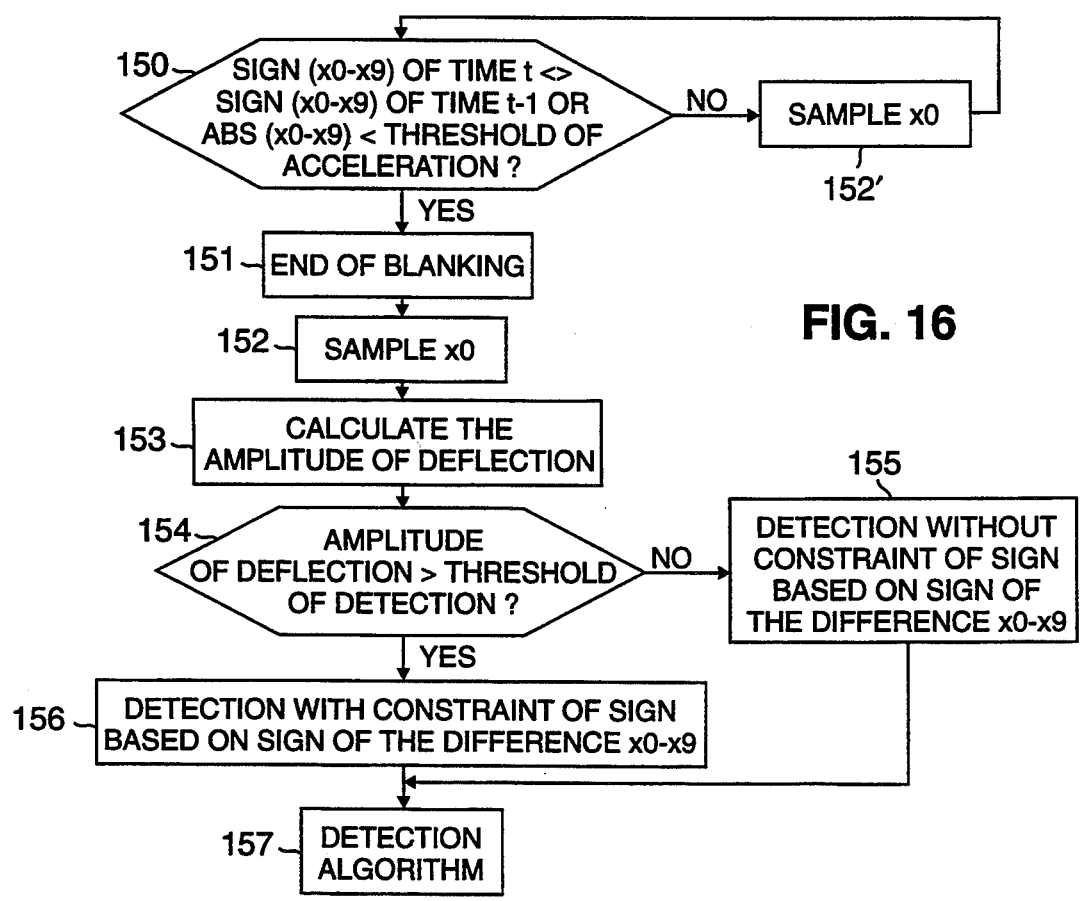
FIG. 16 is a flow chart for the processing of the automatic blanking.

In case of an automatic adjustment of the duration of the blanking, with reference to FIG. 16, the test of end of blanking rests on the double criterion of slope inversion $(x0-x9)$, or slope $(x0-x9)$ becoming very weak, i.e., small. Indeed, if the signs of two consecutive differences $(x0-x9)$ are different or if the absolute value of the difference $(x0-x9)$ becomes less than the threshold of acceleration, one can consider that the signal presents its maximal deflection (step 150, FIG. 16). Once this inversion is found, the algorithm of detection considers the period of blanking as ended and it executes the same test of cross-talk described previously with reference to FIG. 15.

A maximal period during which the inversion has to occur is previously fixed. This is to avoid remaining too long in the blanking if the signal presents an anomaly. This period is called blanking maximum BMAXI (FIG. 14).

As previously described, the principle of detection of a cardiac event rests on the comparison between the slope of the signal for a duration, e.g., 6 to 12 ms, preferably 9 ms, and an adjustable value selected, i.e., programmed, by the physician called threshold of detection.

Many studies show that the amplitude and the form of P waves and R waves vary from time to time as a function notably of the physical activity, the stress, the evolution of the pathology, etc . . . . Consequently, the sensitivity that is adjusted by the physician on the day the pacemaker is implanted can prove to be too low in some cases, which leads to an absence of detection of the spontaneous activity, or too high in other cases, which leads to detecting noise as a cardiac detection. In the two cases, the pacemaker is going to send a stimulation impulse at the end of each cycle of sensing.

In the case of a loss of detection, it is possible with applicant's invention to implement an automatic adjustment of the sensitivity. In this regard, known techniques consider the following. U.S. Pat. Nos. 4,768,511 and 4,766,902 process an automatic sensitivity adjustment by comparison of the amplitude of the signal sensed with two thresholds. The sensitivity is considered as well adjusted if the first threshold is exceeded and not the second, the sensitivity is too high if the two thresholds are exceeded, and the sensitivity is too low if none of the two thresholds is exceeded. The threshold of detection is therefore modified following conditions previously stated. EP patent 0 349 130 and U.S. Pat. No. 4,827,934 use the same principle for the search of a satisfactory sensitivity, but in case of correction of the sensitivity, it is the gain of the circuit of detection, and that is modified, but not the threshold of detection. U.S. Pat. No. 4,708,144 refers to the search of sensitivity following a method that consists in studying the maximal value of the amplitude of the signal to detect, and determining an average with the maximal value of the preceding event. The sensitivity is then modified by a change of gain of the circuit of detection. Another known technique is disclosed copending and commonly assigned U.S. patent application Ser. No. 07/994,725 which is hereby incorporated by reference.

Figure 17:
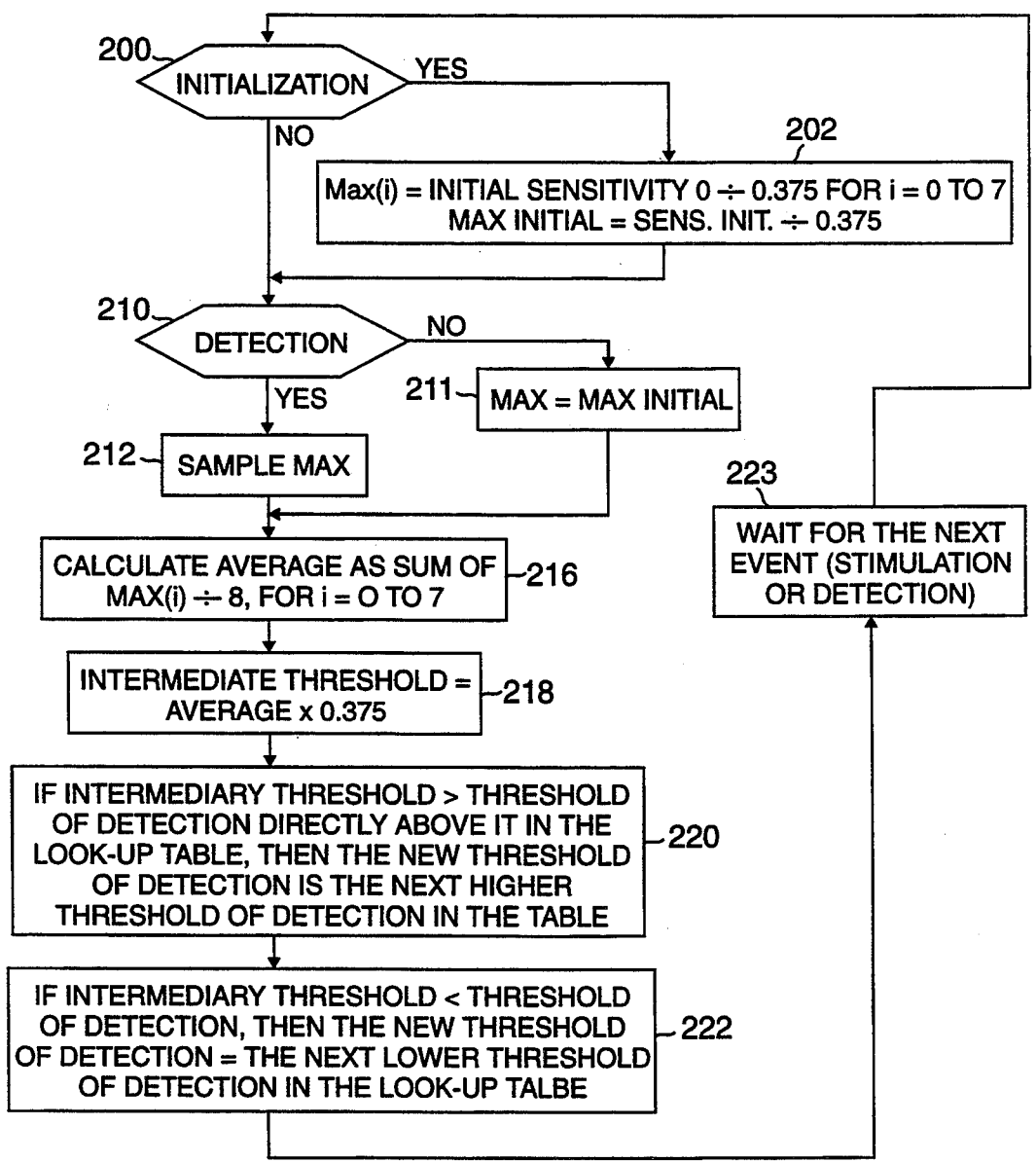
FIG. 17 is a flow chart for the automatic adjustment of the sensitivity.

According to the present invention, with reference to FIG. 17, the automatic adjustment of sensitivity involves studying the maximal value of the absolute value of the difference (x0−x9) after the detection of an event, and calculating the maximal value average of several events previously detected to determine the new sensitivity. To obtain the maximal value, after the detection of an event, a period of search of maximum (PRM), which is fixed in the embodiment described to 48 ms, is launched (step 212), during which the absolute value of the difference (x0−x9) is compared with a value called MAX initialed to zero in the beginning of the PRM period (steps 212, 214). If the absolute value of the difference (x0−x9) is greater than the value MAX, then MAX takes the value of the absolute value of the difference (x0−x9). The value MAX is stored in memory. This operation is realized by microcontroller 4 dedicated to the detection.

At the end of the PRM period, microprocessor 5 reads the value MAX on bus 16 (FIG. 1), and calculates the average of the last eight values MAX stored in memory (step 216). The microprocessor 5 calculates an intermediate threshold as a certain percentage of the average of the eight value MAX (step 218). In the embodiment described, the retained percentage is 37.5%. The microprocessor 5 also possesses in a memory a table in which are found all possible programmable sensitivities as well as thresholds of detection, thresholds of acceleration, frequencies and the corresponding steps of the ADC 3.

If the intermediate threshold is smaller than the programmed detection threshold (step 222), then the new threshold of detection is the next lower threshold in the table relative to the threshold of detection programmed.

If the intermediate threshold is greater than the threshold of detection next greater in the table to the programmed detection threshold (step 220), then the new threshold of detection is the next greater threshold in the table relative to the threshold programmed.

At the initialization (Step 200), the initial sensitivity is programmable by the physician (step 202). By default, its values are preferably 1.0 mV in the atrium an 2.2 mV in the ventricle. The eight value MAX are then initialized to the programmed sensitivity divided by 0.375.

In case of stimulation, the value MAX that is retained corresponds to the value initial MAX, and is the initial sensitivity divided by the retained percentage, i.e., 0.375 in the embodiment described. Following this principle, at the end of eight consecutive stimulations, the programmed sensitivity has for its value the initial sensitivity.

The present invention is suitable for use in, e.g., programmable dual chamber cardiac pacemakers, such as those available from ELA Medical, Montrouge France, under the trademark CHORUS, and compatible intracardial leads, which include known telemetry circuits, stimulation pulse generators, as well as microprocessor and associated storage registers, memory and software programming for cardiac monitoring and stimulation pulse delivery.

Advantages of the present invention include a reduction of the number of external electronic components, and an improved integration of components in the chip (integrated circuit) as a result of the switched capacitors of amplifier 2. Another advantage, linked to the large bandwidth of the filter and to the great dynamics of the amplifier, is that a unique electronic circuit of acquisition and detection of the cardiac activity is used both for the functioning of the cardiac pacemaker, i.e., cardiac event monitoring, and for the sensing of the intracardial ECG for telemetry transmission for external monitoring. Yet another advantage of the present invention is an improved detection algorithm that is more adaptive to sensed signals than prior techniques. These advantages arise input from the large bandwidth filter and the large dynamic amplifier which provide a non altered cardiac signal that is digital and can be easily and accurately processed.

One skilled in the art will appreciate that the present invention can be practiced by other than the described embodiments, which are presented for purposes of illustration and not of limitation.

We claim:

1. An apparatus for acquiring and detecting intracardial cardiac activity signals comprising:

a passive filter having a passband width of from 0.1 Hz to 80 Hz, an input for receiving cardiac activity signals, and an output for providing filtered signals;

an amplifier integrated circuit including switched capacitors and having an input for receiving the filtered signals, a gain lower than 50, and an output for providing amplified signals in a dynamic range of approximately 0.8V;

an analog-to-digital converter with delta modulation, having a controllable frequency and step for converting an input analog signal to a digital value, an input for receiving the amplified signals, and an output for providing digital values corresponding to the amplified signals;

processor means for processing the digital values; and means for detecting spontaneous cardiac events based on the processed digital values.

2. The apparatus of claim 1 characterized in that the analog-to-digital converter controllable frequency further comprises at least two frequencies that are separately selectable.

3. The apparatus of claim 2 wherein the two frequencies are approximately 1 kHz, and approximately 4 kHz, and the processor means further comprises an output command signal for controlling the analog-to-digital converter to operate at one of the two frequencies.

4. The apparatus of claim 1 wherein the amplifier circuit gain and dynamic range are selected to detect atrial and/or ventricular spontaneous events, and further comprising means for measuring the parameter of efficiency of stimulation, and means for transmitting an intracardial ECG by telemetry based on said digital values.

5. The apparatus of claim 4, further comprising means for automatically adjusting the period of blanking.

6. The apparatus of claim 4, further comprising means for automatically adjusting the sensitivity.

7. The apparatus of claim 6 wherein the automatic sensitivity adjustment means further comprises means for determining the absolute value of the maximal amplitude variation of the signal sensed during a plurality of successive first durations beginning with a detected spontaneous cardiac event and ending a second period following said detected event; and
means for determining the maximal amplitude variation for a plurality of consecutive cardiac events; and
means for calculating the sensitivity as a first percentage of the average of the plurality of maximal values.

8. The apparatus of claim 7, wherein the automatic sensitivity adjustment means further comprises means for providing an initial sensitivity value based on a programmed value multiplied by a constant value, wherein the maximal amplitude determining means determines the maximal value following a stimulated cardiac event as the initial sensitivity value.

9. The apparatus of claim 8 wherein the constant value is the inverse of the first percentage, the first percentage is on the order of 37.5%, and the first plurality of consecutive cardiac events is eight cardiac cycles.

10. The apparatus of claim 4 wherein the processor means further comprises:
means for determining an absolute value of the variation of amplitude of a plurality of the digital values sensed during a first duration, the first duration being selected in the range of from 6 to 12 ms;
means for comparing said determined absolute value to an acceleration threshold; and
means for selecting the frequency and step of analog-to-digital converter based on said comparison.

11. The apparatus of claim 1 wherein the processor means further comprises means for determining an absolute value of the variation of amplitude of a plurality of digital values of the signal sensed during the first duration, the first duration being selected in the range from 6 to 12 ms, means for comparing said absolute value to a detection threshold, and means for determining a detection of an atrial or ventricular spontaneous cardiac event based on said comparison.

12. The apparatus of claim 11 further comprising:
means for controlling the absolute value determining means to determine a first sign of a variation of amplitude and first amplitude variation and a second sign of a variation of amplitude and second amplitude variation, the first sign and first amplitude being based on a first plurality of digital values sensed during said first duration at a time before the end of an absolute refractory period, and the second sign and second amplitude being based on a second plurality of digital values sensed during said first duration at a time after the end of an absolute refractory period;
second means for comparing the first and second signs and amplitudes; and
means for indicating a spontaneous cardiac event in response to the absolute value of the second amplitude being greater than the detection threshold and the second sign being of opposite polarity to the first sign.

13. The apparatus of claim 11 wherein the processor means further comprises a microcontroller dedicated to perform numerical processing of the digital values to detect intracardial cardiac activity.

14. The apparatus of claim 11 further comprising:
means for determining an amplitude of cross-talk in response to an identified atrial stimulation;
means for providing a ventricular blanking interval in response to an atrial stimulation; and
means for automatically adjusting the ventricular blanking interval based on said determined cross-talk amplitude following an atrial stimulation.

15. The apparatus of claim 14 further comprising means for controlling the absolute value determining means to determine the sign of the variation of amplitude for the first plurality of digital values sensed during each of a plurality of successive first durations, said plurality of first durations beginning after the atrial stimulation, wherein the adjusting means adjusts the end of the ventricular blanking interval to correspond to the occurrence in time of the one first duration having a sign that is the inverse of the sign of the preceding first durations of said plurality of first durations.

16. The apparatus of claim 14 further comprising;
means for determining a value VLB as the base line digital value at the moment of stimulation in response to an atrial stimulation;
means for determining a value VFB as the digital value at the end of the ventricular blanking interval;
wherein the absolute value determining means further comprises:
means for determining the difference between the values VFB and VLB as the deflection and the sign of deflection;
means for comparing the determined deflection to the deflection threshold;
means for determining whether the determined deflection is greater than the detection threshold and in response thereto determining the absolute value and sign of the variation of amplitude for a plurality of digital values sensed during a first duration at the end of the ventricular blanking interval, wherein the identifying means identifies a ventricular event based on the comparison of said absolute amplitude value and said detection threshold.

17. The apparatus of claim 16 wherein the identifying means further comprises means for identifying a ventricular event based on the comparison of said absolute amplitude value and said detection threshold and said sign of said variation of amplitude being the same as the sign of the determined deflection.

18. A method of processing electrical signals corresponding to intracardiac activity comprising:
(a) filtering the electrical signals to suppress frequencies below 0.1 Hz and above 80 Hz;
(b) providing an amplifier integrated circuit having switched capacitors, a dynamic range of 0.8V and a gain of less than 50, and amplifying the filtered signal by said amplifier;

(c) providing a digital to analog converter (ADC) having delta modulation and a controllable frequency and step;

(d) selecting the ADC frequency and step based on previously sensed amplified signals;

(e) converting said amplified signals to digital values by said ADC at the selected frequency and step; and (f) processing said digital values to identify the occurrence of spontaneous atrial and/or ventricular cardiac events.

19. The method of claim 18 wherein step (d) further comprises selecting the frequency to be one of 1.0 kHz and 4.0 kHz.

20. The method of claim 18 further comprising processing selected ones of said digital values to measure the parameter of efficiency.

21. The method of claim 18 further comprising telemetering a portion of said digital values to a remote location for display of an intracardial ECG.

22. The method of claim 18 further comprising processing selected ones of said digital values and automatically adjusting a period of blanking following a cardiac stimulation.

23. The method of claim 18 further comprising processing selected ones of said digital values and automatically adjusting the sensitivity.

24. The method of claim 23 wherein automatically adjusting the sensitivity further comprises determining the absolute value of the maximal amplitude variation of a plurality of digital values sensed during a first duration for a plurality of successive first durations beginning with a detected spontaneous cardiac event and ending a second period following said detected event;

determining the maximal amplitude variation for a plurality of consecutive cardiac events; and calculating the sensitivity as a first percentage of the average of the plurality of maximal values.

25. The method of claim 24, wherein automatically adjusting the sensitivity further comprises providing an initial sensitivity value based on a programmed value multiplied by a constant value, and determining the maximal amplitude value following a stimulated cardiac event as the initial sensitivity value.

26. The method of claim 25 further comprising selecting the constant value to be the inverse of the first percentage, selecting the first percentage to be on the order of 37.5%, and selecting the plurality of consecutive cardiac events to be eight cardiac cycles.

27. The method of claim 18 wherein step (f) further comprises:

determining an absolute value of the variation of amplitude of a plurality of digital values sensed during a first duration, the first duration being selected from between 6 and 12 ms;

comparing the determined absolute value to an acceleration threshold; and performing step (d) to control the frequency and step of the analog to digital converter in response to said comparison.

28. The method of claim 18 wherein step (f) further comprises:

(i) determining an absolute value of the variation of amplitude of a plurality of digital values sensed during a first duration, the first duration being selected from between 6 and 12 ms;

(ii) comparing the determined absolute value to a detection threshold; and (iii) determining the occurrence of a spontaneous atrial and/or ventricular cardiac event based on said comparison.

29. The method of claim 28 wherein step (f) further comprises:

determining a first sign of a variation of amplitude and first absolute amplitude variation and a second sign of a variation of amplitude and second absolute amplitude variation, the first sign and first absolute amplitude being based on a first plurality of digital values sensed during said first duration at a time before the end of an absolute refractory period, and the second sign and second absolute amplitude being based on a second plurality of digital values sensed during said first duration at a time after the end of an absolute refractory period;

comparing the first and second signs and amplitudes; and indicating a spontaneous cardiac event in response to the absolute value of the second amplitude being greater than the detection threshold and the second sign being of opposite polarity to the first sign.

30. The method of claim 28 further comprising providing a microcontroller that is dedicated to numeric processing of the digital values to identify spontaneous cardiac events.

31. The method of claim 28 further comprising:

determining an amplitude of cross-talk in response to an identified atrial stimulation;

providing a ventricular blanking interval in response to an atrial stimulation; and automatically adjusting the ventricular blanking interval based on said determined cross-talk amplitude following an atrial stimulation.

32. The method of claim 31 further comprising determining the sign of the variation of amplitude for the first plurality of digital values sensed during each of a plurality of successive first durations, said plurality of first durations beginning after the atrial stimulation, wherein the adjusting step adjusts the end of the ventricular blanking interval to correspond to the one first duration having a sign that is the inverse of the sign of the preceding first durations of said plurality of first durations.

33. The method of claim 31 further comprising;

determining a base line digital value VLB in response to an atrial stimulation as the digital value at the moment of stimulation;

determining a digital value VFB as the digital value at the end of the ventricular blanking interval;

determining the difference between the values VFB and VLB as the deflection and the sign of deflection;

comparing the determined deflection to the deflection threshold; and determining whether the determined deflection is greater than the detection threshold and in response thereto determining the absolute value and sign of the variation of amplitude for a plurality of digital values sensed during a first duration at the end of the ventricular blanking interval, and identifying a ventricular event based on the comparison of said absolute amplitude value and said detection threshold.

34. The method of claim 33 wherein the identifying step further comprises identifying a ventricular event based on the comparison of said absolute amplitude value and said detection threshold and said sign of said variation of amplitude being the same as the sign of the determined deflection.

35. A circuit for processing electrical signals corresponding to intracardiac activity for an implantable cardiac pacemaker comprising:
- a band pass filter having low cutoff frequency at about 0.1 Hz and a high cutoff frequency at about 80 Hz;
- an amplifier integrated circuit having switched capacitors, a low gain of less than 50, and a dynamic range on the order of 0.8V, said amplifier being connected to the filter to amplify the filtered electrical signals;
- a digital to analog converter (ADC) having delta modulation and a controllable frequency and step for converting an analog signal to a digital value, said ADC being controlled to convert said amplified signals to digital values.

36. The circuit of claim 35 wherein the analog to digital converter is controllable to have at least a first frequency and a second frequency, and a first step and a second step.

37. The circuit of claim 36 wherein the first frequency is 1.0 kHz and the second frequency is 4.0 kHz.

38. The circuit of claim 35 wherein the amplifier is a differential amplifier.

39. An implantable cardiac monitoring device comprising:
- a lead for receiving electrical signals corresponding to intracardiac electrical activity;
- a band pass filter having low cutoff frequency at about 0.1 Hz and a high cutoff frequency at about 80 Hz, the filter having an input connected to said lead and an output;
- an amplifier integrated circuit having switched capacitors, a low gain of less than 50, and a dynamic range on the order of 0.8V, said amplifier being connected to the filter output to amplify the filtered electrical signals;
- a analog to digital converter (ADC) having delta modulation and a controllable frequency and step for converting an analog signal to a digital signal, said ADC being controlled to convert said amplified signals to digital values.

40. The device of claim 39 further comprising:
processing means for processing the digital values to identify spontaneous cardiac activity; and
means for telemetering the digital values out of the pacemaker to provide a intra cardiac ECG for display.

41. The apparatus of claim 40 wherein the cardiac monitoring device is a pacemaker.

* * * * *